(12) United States Patent
Montero-Julian et al.

(10) Patent No.: US 7,101,678 B1
(45) Date of Patent: Sep. 5, 2006

(54) METHOD FOR DETECTING OR QUANTIFYING BASOPHILS AND EOSINOPHILS

(76) Inventors: Felix Montero-Julian, 6, rue Marie Louise, Le Marie Louise, Bât C, 13008 Marseilles (FR); Anne M. Morel Montero, 6, rue Marie Louise, Le Marie Louise, Bât C, 13008 Marseilles (FR); Hervé Brailly, L'amandiére Le Clos, 13360 Roquevaire (FR); Michel Delaage, 16 rue Adophe Thiers, 13001 Marseilles (FR)

(*) Notice: Subject to any disclaimer, the term of this patent is extended or adjusted under 35 U.S.C. 154(b) by 0 days.

(21) Appl. No.: 09/787,006
(22) PCT Filed: Sep. 9, 1999
(86) PCT No.: PCT/FR99/02145
§ 371 (c)(1),
(2), (4) Date: Sep. 10, 2001
(87) PCT Pub. No.: WO00/16103
PCT Pub. Date: Mar. 23, 2000

(30) Foreign Application Priority Data
Sep. 10, 1998 (FR) .................... 98 11456

(51) Int. Cl.
*G01N 33/567* (2006.01)
*G01N 33/53* (2006.01)
(52) U.S. Cl. ............... 435/7.21; 435/7.1; 435/7.2; 435/7.24
(58) Field of Classification Search ............... 435/7.21, 435/4, 6, 7.1, 7.2, 7.4, 7.5, 7.6, 7.7, 7.71, 435/7.72, 7.8, 7.9, 7.91, 7.92, 7.93, 7.94, 435/7.95, 973, 512, 517, 578, 519, 547, 548, 435/3
See application file for complete search history.

(56) References Cited

U.S. PATENT DOCUMENTS 5,096,704 A    3/1992   Coffman et al.
5,693,323 A *  12/1997  Ames et al. .............. 424/145.1
5,776,709 A *  7/1998   Jackson et al. ............ 435/7.24
6,018,032 A *  1/2000   Koike et al. ........... 530/388.22
6,537,764 B1 * 3/2003   Gerard et al. .............. 435/7.21
6,599,914 B1 * 7/2003   Schleimer et al. .......... 514/291

FOREIGN PATENT DOCUMENTS

EP       0 811 691 A1   12/1997
WO       WO 97/48418 A1 12/1997

OTHER PUBLICATIONS

Matsumoto et al., "CD44 and CD69 represent different types of cell-surface activation markers for human eosinophils", America journal of respiratory cell and molecular biology, 18(6), pp. 860-866, 1998.*

(Continued)

*Primary Examiner*—Long V. Le
*Assistant Examiner*—Ann Y. Lam
(74) *Attorney, Agent, or Firm*—Browdy and Neimark, PLLC

(57) ABSTRACT

The invention concerns a method for detecting or quantifying eosinophils and basophils, which consists in contacting a sample possibly containing said eosinophils or basophils with an IL-5 anti-receptor (alpha-chain) monoclonal antibody which does not interfere with IL-5 fixation to its receptor and does not inhibit the IL-5 biological activity to detect and, if required to quantify eosinophils and basphils. The invention also concerns a kit for detecting or quantifying eosinophils or basophils and an anti-IL5R antibody.

18 Claims, 9 Drawing Sheets

OTHER PUBLICATIONS

Figure 1:
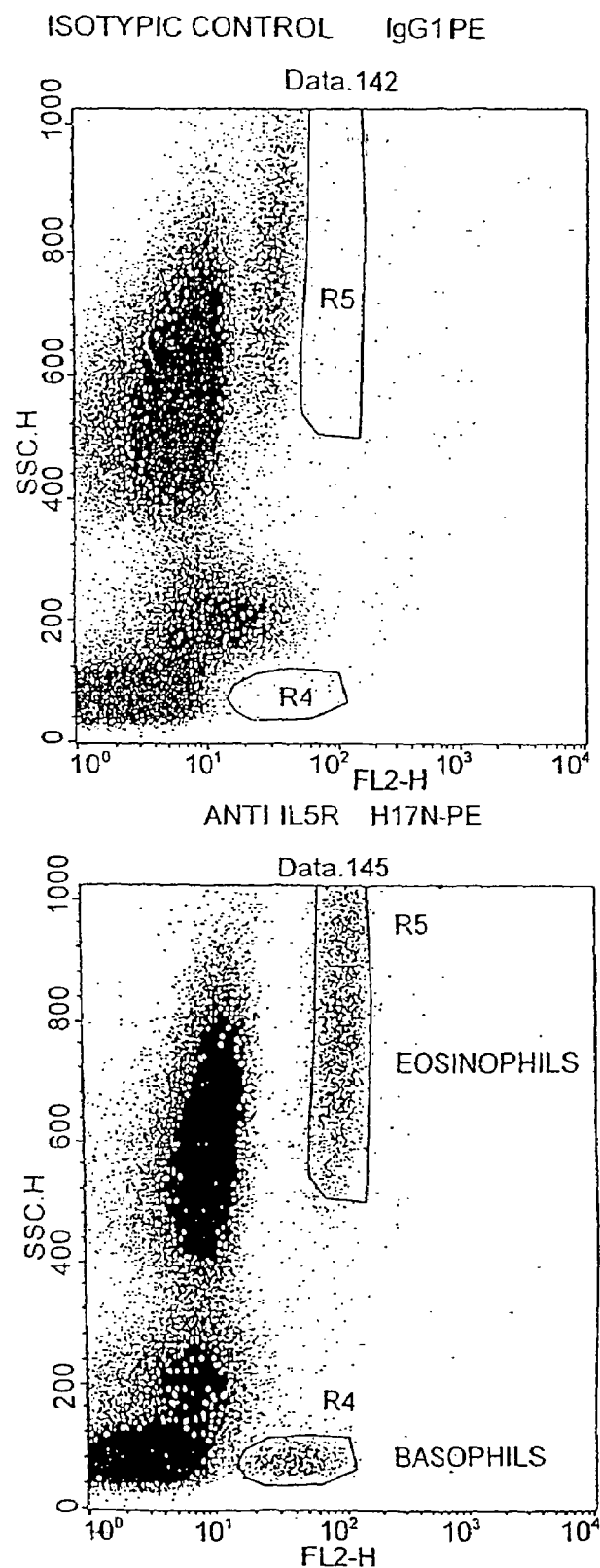

Monahan et al., "Attenuation of IL-5 mediated signal transduction, eosinophil survival, and inflammatory mediator", Journal of Immunology, vol. 159(8), pp. 4024-4034, 1997.*

Fureder et al., "The surface membrane antigen phenotype of human blood basophils", Allergy: European Journal of Allergy and Clinical Immunology, (1994), 49/10, ppl. 861-865.*

Patent Abstract, WO 00/16103, published Mar. 17, 2000, applicant Immunotech SA, and p. 2 of patent.

Wolfgang Hübl, et al., "Evaluation of Automated Basophil Counting by Using Fluorescence-Labelled Monoclonal Antibodies", Journal of Clinical Laboratory Analysis, vol. 10, pp. 177-183, 1996.

Takemasa Nakagawa et al., "Flow-Cytometric Analysis of Hman Basophil Degranulation" ALLERGY, vol. 36, pp. 39-47, 1981.

Pierre Gane et al., "Flow Cytometric Monitoring of Allergen Induced Basophil Activation", CYTOMETRY, vol. 19, pp. 361-365, 1995.

Qiyu Sun et al., "Monoclonal Antibody 7G# Recognizes the $N$-Terminal Domain of the Human Interleukin-3 (IL-3) Receptor α-Chain and Functions as a Specific IL-3 Receptor Antagonist", BLOOD, vol. 87, No. 1, pp. 83-92, 1996.

* cited by examiner

METHOD FOR DETECTING OR QUANTIFYING BASOPHILS AND EOSINOPHILS

The present application relates to a novel process for the detection or quantification of basophils and eosinophils in healthy or sick persons, the processes for the preparation of the reagents required and the implementation thereof, particularly in the form of kits.

It is difficult to study eosinophils and basophils because of the very small number of these cells in the blood, that is, from 1% to 3% and less than 1% respectively. However, their number may increase considerably in certain pathological states such as parasitic infections, allergic and asthmatic conditions or certain leukaemias.

It has been shown that eosinophils play a very important part in chronic allergic asthma. Eosinophils infiltrate the respiratory passages where they may be activated and may degranulate. The release of the granular contents, enzymes and basic proteins causes damage to the bronchial epithelium. Some reports also mention eosinophil dysfunction.

The bridging of specific IgEs present on basophils by various allergens such as pneumoallergens, venoms, food proteins or medicinal products may lead to the release of the mediators contained in the granules or neoformed and capable of inducing anaphylactic shock.

In order to understand the condition of an individual and to assess his susceptibility to exogenous agents, it is important therefore to count the eosinophils and basophils and to measure the proportion of those which are capable of activation by a particular agent.

The methods of counting basophils and eosinophils are based on staining the granules (manual counting) with, for example, ortho-toluidine blue for basophils and with eosine for eosinophils, their size and their particle size distribution, or based on differential immunophenotyping of their cell surface. These methods are unwieldy, time-consuming and not very specific. They have a high level of uncertainty and considerable statistical errors because of the small number of these cell types. Moreover, most of these methods are unsuitable for analysing the degree of activation of these cells.

For all these reasons, it would be desirable to have products and processes by means of which eosinophils and basophils can be detected and quantified more specifically, whether or not they have been activated.

Various processes using a flow cytometer have been described for the detection of eosinophils and basophils (see, for example, Nakagawa et al., (1981) Allergy, 36; pp 39–47; Gane et al., (1995) Cytometry 19; pp 361–365; Hübl et al., (1996) J. Clin. Lab. Analysis 10, 177–183).

One of the main problems faced when studying basophils and eosinophils by flow cytometry is the distinct separation between the positive cells and the negative cells. Some authors use a remarkable characteristic of eosinophils, their autofluorescence, to identify them more precisely. However, certain clinical samples exhibit very high autofluorescence of monocytes, neutrophils and lymphocytes. The great variability in the particle size distribution of eosinophils should also be emphasised here, this being reflected in the fact that the zone of the scatter diagram (distribution as a function of size and particle size distribution) corresponding to these cells is spread out. On the scatter diagram, the basophils are situated on the border between the lymphocytes and monocytes.

Leucocytes express proteins on their surface characterised in terms of CDs (Cluster of Differentiation) by groups of antibodies which recognise them. The expression of several CDs on the same cell may enable the cell to be characterised. The same CD may be expressed on different cell types. For this reason, most of the flow cytometry processes use mixtures of antibodies that recognise several of these CDs as markers of basophils and eosinophils.

For example, the use of two antibody mixtures, anti-CD2, anti-CD14, anti-CD16 and anti-CD19 on the on hand, and anti-CD32, anti-CD25, anti-IgG1 and anti-IgG4 on the other hand makes it possible to detect basophils with a flow cytofluorimeter. The anti-CD2 antibodies detect T cells, the anti-CD19 antibodies make it possible to detect B cells, and the anti-CD14 antibodies detect mainly monocytes but also granulocytes. CD16, an IgG type III receptor, is expressed on neutrophils, certain T (NK) cells and on monocytes. CD32, an IgG type II receptor, is expressed on monocytes, neutrophils and B lymphocytes. CD25 is a marker of T and B cell activation, and a marker of macrophage activation. Several of these markers are shared by different types of leucocytes. Basophils and eosinophils are minority populations of leucocytes. For this reason, most of the data on basophils and eosinophils have been obtained from purified cells. For example, it was possible to study the basophils of individuals with chronic myeloid leukaemia after several purification steps using monoclonal antibodies followed by lysis of the red corpuscles by complement. However, this process is impracticable for routine use because it is long and requires a large volume of blood.

Other processes for the detection of basophils use an anti-IgE antibody or an anti-receptor antibody with a high affinity for IgE. These processes do not, however, permit a clear identification of basophils because small amounts of high-affinity IgE receptor have been revealed on monocytes, and eosinophils and B cells may carry IgE on their surface. Moreover, bridging of IgE or of their receptors on the surface of basophils by the antibodies used as a probe may lead to cell activation altering the properties of the membrane. It has been shown that the activation of basophils by an allergen brings about a reduction in the binding of an anti-IgE antibody.

It would be desirable, therefore, to be able to count eosinophils and basophils easily and without risk of error, even amongst the other cell populations of human blood, and to measure the proportion of those capable of being activated by a particular agent.

In response to the problem of diagnosing and treating diseases such as chronic bronchial asthma or atopic dermatitis, EP-A-0 811 691 proposes antibodies of various types: monoclonal, humanised etc., directed against the α chain of the interleukin-5 receptor which blocks the activity of this cytokine. It also proposes a process for the detection of eosinophils. But the use of antibodies neutralising the biological activity of IL-5 gives disappointing results in the flow cytometry analysis. The specific signal obtained on eosinophils, even if they have been purified, cannot be distinguished from the signal obtained with a control antibody (background).

When characterising a group of monoclonal antibodies directed against the interleukin-5 receptor (IL-5R), the Applicant discovered that, surprisingly, basophils and eosinophils amongst other cell populations of human or animal blood could be detected in isolation and together by using certain antibodies specific for the alpha chain of the interleukin-5 receptor and that these same cells could also be counted, if desired. The Applicant has shown, by bio-assays on TF1 cells which are dependent on IL-5 for their survival, that these selected antibodies did not inhibit the growth of these cells.

Moreover, the Applicant has also shown that the receptor bound to these antibodies and immobilised on a solid phase is still capable of fixing marked IL-5.

For this reason, the present application provides a process for the detection or quantification of eosinophils and basophils, characterised in that it comprises bringing a sample optionally containing said eosinophils or basophils into contact with an IL-5 anti-receptor (alpha chain) monoclonal antibody which does not interfere with the fixing of IL-5 to its receptor and which does not inhibit the biological activity of IL5 in order to detect and, if desired, quantify the eosinophils and basophils.

The invention uses, therefore, an IL-5 anti-receptor (alpha chain) monoclonal antibody and the expression of the alpha chain of the IL-5 receptor as a specific marker of eosinophils and basophils. It was observed that this marking was specific for these blood cells and that none of the B or T cells, monocytes or neutrophils was marked.

These antibodies may therefore be used for counting basophils and eosinophils accurately and precisely under all circumstances.

The sample optionally containing said eosinophils or basophils may be, for example, a blood sample originating in particular from a sick person, preferably suffering from an allergy or parasitic disorder.

According to the process described above, the IL-5 anti-receptor monoclonal antibody is an antibody which does not interfere with the fixing of IL-5 to its receptor and which does not inhibit the biological activity of IL-5.

The absence of inhibition of the biological activity of IL-5 may be shown by bio-assay on TF1 cells which are dependent on IL-5 for their survival, the antibodies according to the invention not inhibiting the growth of these TF1 cells.

Under preferred conditions of carrying out the process described above, the IL-5 anti-receptor monoclonal antibody is an antibody which does not interfere with IgE. The expression "does not interfere with IgE" means an antibody which does not prevent the binding of an allergen or of another anti-IgE antibody to these surface IgE.

Under further preferred conditions of carrying out the process described above, the IL-5 anti-receptor monoclonal antibody is an antibody which does not interfere with cell activation of eosinophils or basophils. The expression "does not interfere with cell activation of eosinophils or basophils" means an antibody which, by virtue of its binding to the surface of the cell, does not induce or inhibit the appearance of a surface activation marker of basophils or eosinophils.

Under yet further preferred conditions of carrying out the process described above, the detection and, if desired, the quantification of eosinophils and basophils uses a flow cytometer or optical scanning cytometer.

Human basophils express on their surface markers such as CD11, CD13, CD18, CD26; CD31, CD32, CD33, CD40, CD43, CD44, CD45, CD49d, CD54, and eosinophils express on their surface CD15, CD32, CD44, CD49d, CD52, CD65, CD66, CD67. On the other hand, neither basophils nor eosinophils express CD3, CD14, CD16, CD19. These lists of markers are not exhaustive.

For this reason, the present application also provides an above process characterised in that, moreover, the sample is brought into contact with one or preferably more than one other monoclonal antibody directed against other markers making it possible to exclude cell types other than eosinophils or basophils. Thus, it is possible to distinguish lymphocytes, monocytes and neutrophils from eosinophils and basophils.

Exclusion markers are therefore used to improve still further the accuracy of counting by excluding erratic events. The present application provides, in particular, an above process characterised in that the other monoclonal antibodies are directed against the markers CD3, CD 16 and CD 19 which make it possible to exclude erratic events.

The invention permits the detection and specific quantification of activated or non activated basophils and eosinophils. It has been shown recently that CD63, a lysosomal protein of the tetraspan family and initially described as a platelet activation marker, was also present in the granules of basophils and neutrophils. The expression of CD63 on the cell surface is calcium-dependent. When basophils are activated, the CD63 expressed on the surface may be recognised by a specific antibody. The intensity of marking is a function of the number of cells activated.

For this reason, the present application also provides an above process characterised in that the detection or quantification of activated basophils is carried out by also bringing the sample into contact with one or more other monoclonal antibodies directed against basophil activation markers and particularly against the CD63 antigen.

Similarly, the present invention also provides an above process characterised in that the detection or quantification of activated eosinophils is carried out by also bringing the sample into contact with one or more monoclonal antibodies directed against eosinophil activation markers and more particularly against the CD69 antigen.

Moreover, it is possible to detect and count basophils and eosinophils separately if an additional means of discrimination is available such as the diffusion of light in flow cytometers where eosinophils are distinguished from basophils by a much higher side scatter value, the peroxidase activity characteristic of eosinophils which is revealed by using precipitating substrates such as DAB (diaminobenzidine) or fluorescent substrates such as dichlorofluorescein diacetate, a non-fluorescent substrate converted to highly fluorescent 2',7'-dichlorofluorescein.

The present application also provides an anti-IL-5R antibody characterised by:

the absence of interference with the fixing of IL-5 to its receptor, the absence of interference with IgE, the absence of interference with cell activation of eosinophils or basophils, the absence of inhibition of the biological activity of IL-5.

An advantageous embodiment of the invention consists in the use of a mixture of antibodies directed, on the one hand, against IL-5R, with or without "specific" markers for T and B lymphocytes, NK cells, monocytes and neutrophils and, if activated eosinophils or basophils are of interest, on the other hand, a marker of basophil and eosinophil activation. The cell activation marker may be a specific antibody for a protein appearing on the surface of the cell membrane after activation, or the detection of oxidative enzyme activity. The latter makes it possible to detect and, optionally, to quantify cell activation.

For this reason, the present application also provides kits targeted for different applications, said kits having, as their basis, an anti-IL-5R monoclonal antibody, preferably of mouse, rat or rabbit, or genetically modified, and primarily a kit for the detection or quantification of eosinophils or basophils containing
   at least one anti-IL-5R monoclonal antibody as defined above conjugated to a first fluorochrome,
   a mixture of antibody markers for lymphocytes, monocytes and neutrophils, conjugated to a second fluorochrome,
and a kit for the detection and quantification of activated eosinophils and basophils containing
   at least one anti-IL-5R monoclonal antibody as defined above conjugated to a first fluorochrome,
   a mixture of antibody markers for lymphocytes, monocytes and neutrophils, conjugated to a second fluorochrome and
   antibodies directed against activation markers and conjugated to a third fluorochrome.

The present application also provides an above kit, characterised in that it also includes a specific substrate for the oxidative activity of eosinophils.

The present application also provides a kit for the detection or quantification of the oxidative activity of eosinophils or basophils containing
   at least one anti-IL-5R monoclonal antibody as defined above conjugated to a first fluorochrome,
   a mixture of antibody markers for lymphocytes, monocytes and neutrophils conjugated to a second fluorochrome,
   a marker substrate for the oxidative activity of eosinophils or basophils.

The preferred conditions for carrying out the processes described above also apply to the other subject matter of the invention mentioned above.

Finally, the present application provides an above process, antibody or kit, characterised in that the IL-5 anti-receptor monoclonal antibody is an antibody of the IgG1 type, the corresponding hybridoma of which was lodged with the Collection Nationale de Culture de Micro-organismes (CNCM) under no. 1-2068.

The invention may be applied in the test, by clinical and pharmaceutical laboratories, of the response of basophils or eosinophils to different types of degranulating agents (allergens, chemicals, parasites etc) in order to make a diagnosis or to monitor desensitisation, or to reveal the capacity of new molecules to modify the degranulation of basophils or eosinophils and for studying allergic, parasitic and leukaemic pathologies.

The examples below illustrate the present application.

FIG. 1 is an illustration of a dot plot obtained with the anti-IL-5R H17N (B) monoclonal antibody and an isotype control (A) conjugated to phycoerythrin. The abscissas represent the intensity of fluorescence expressed on a logarithmic scale, and the ordinates represent side scatter.

The polygons labelled R4 and R5 represent basophils and eosinophils respectively.

Figure 2A:
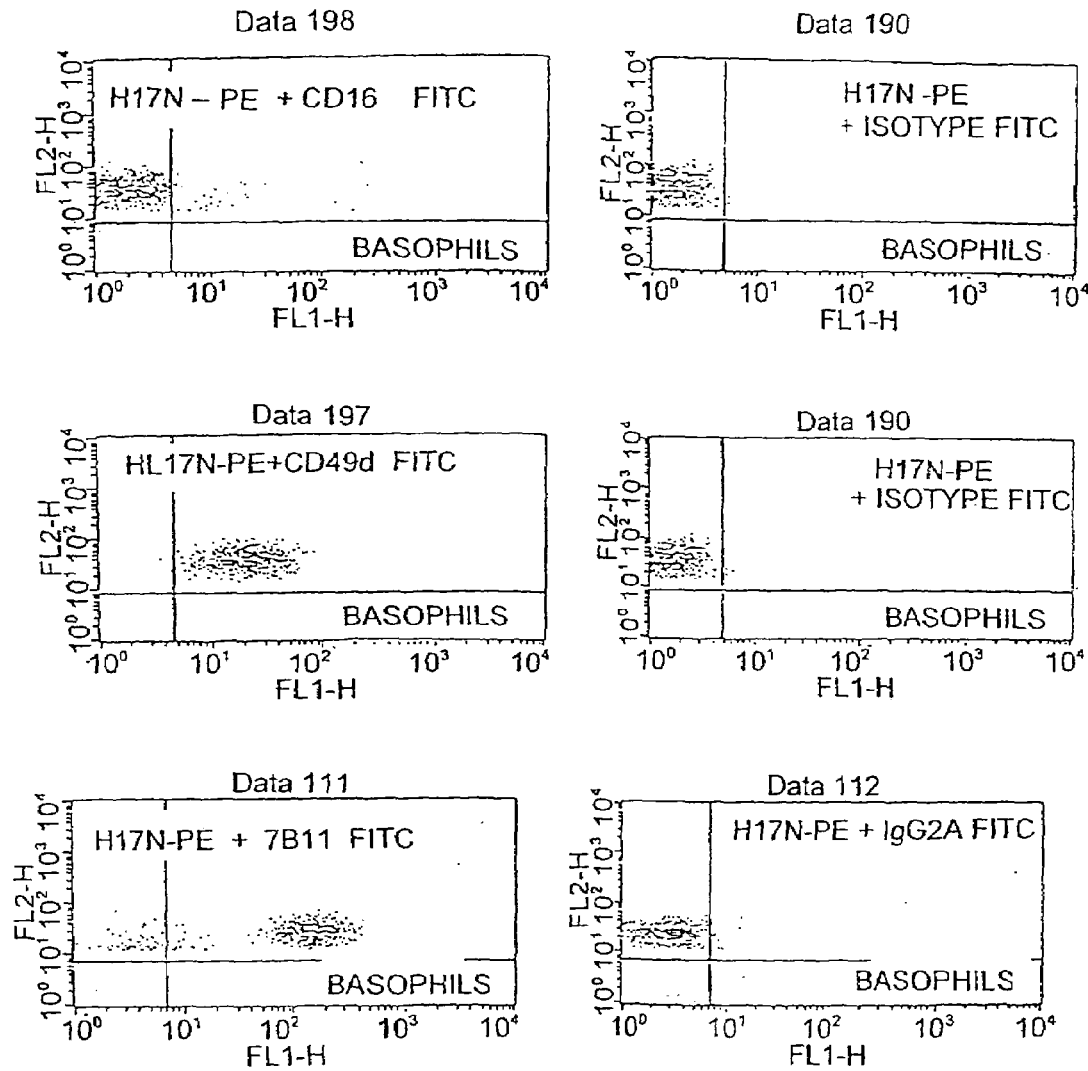
Figure 2:
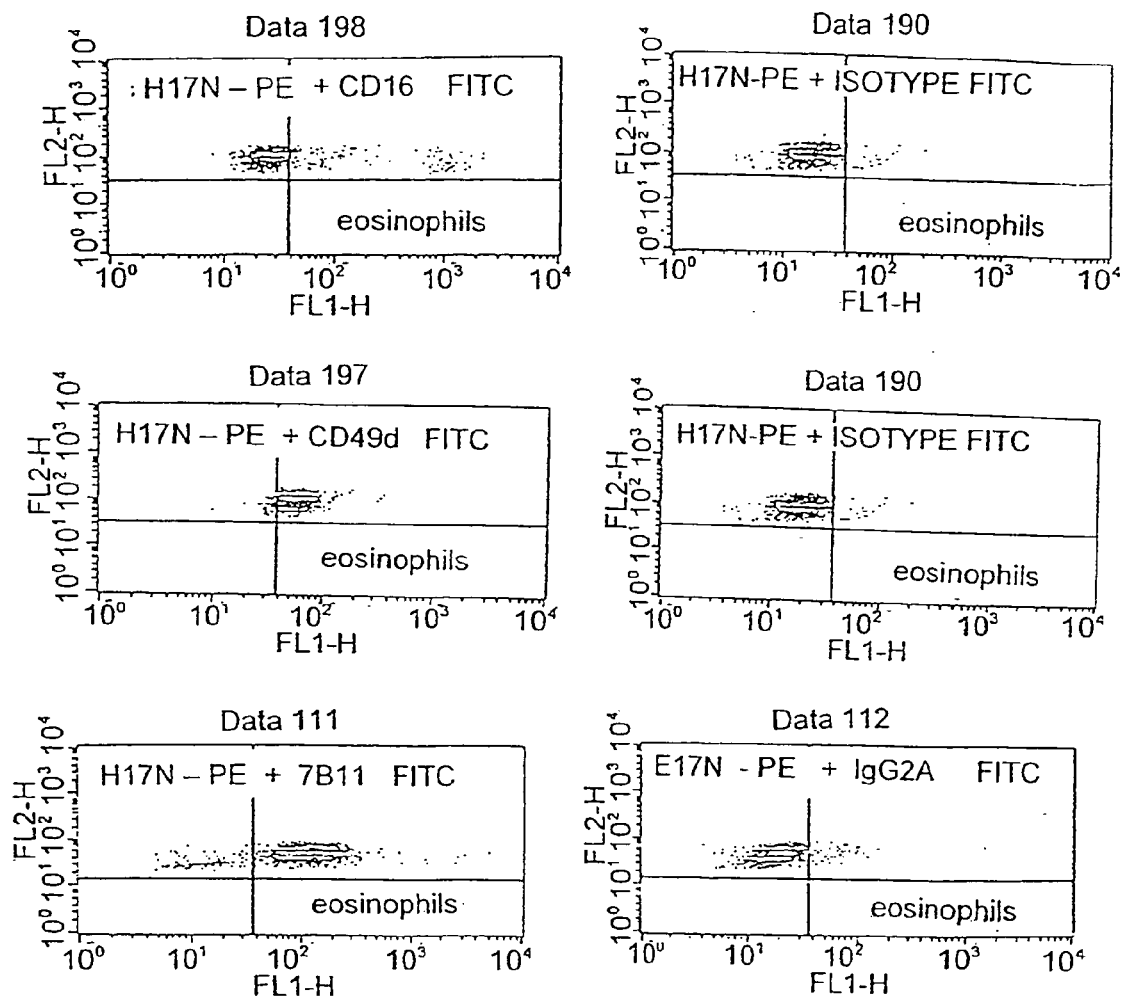

FIGS. 2A and 2B illustrate a double marking obtained with the anti-IL-5R antibody conjugated to phycoerythrin for basophils and eosinophils respectively. The abscissas represent the fluorescence emitted by fluorescein (FITC) and the ordinates the fluorescence emitted by phycoerythrin (PE).

The left-hand dot plot represents the double marking between the anti-IL-5R-PE and an antibody specific for another marker conjugated to FITC. The right-hand dot plot represents the marking obtained with an isotype control of the anti-IL-5R-PE.

The markers used are, from top to bottom, anti-CD16 (this marker is present on neutrophils, NK cells, Kupffer cells and a sub-population of macrophages), anti-CD49d (alpha 4 chain of integrins expressed on basophils and eosinophils but also on lymphocytes, monocytes and thymocytes).

Figure 3:
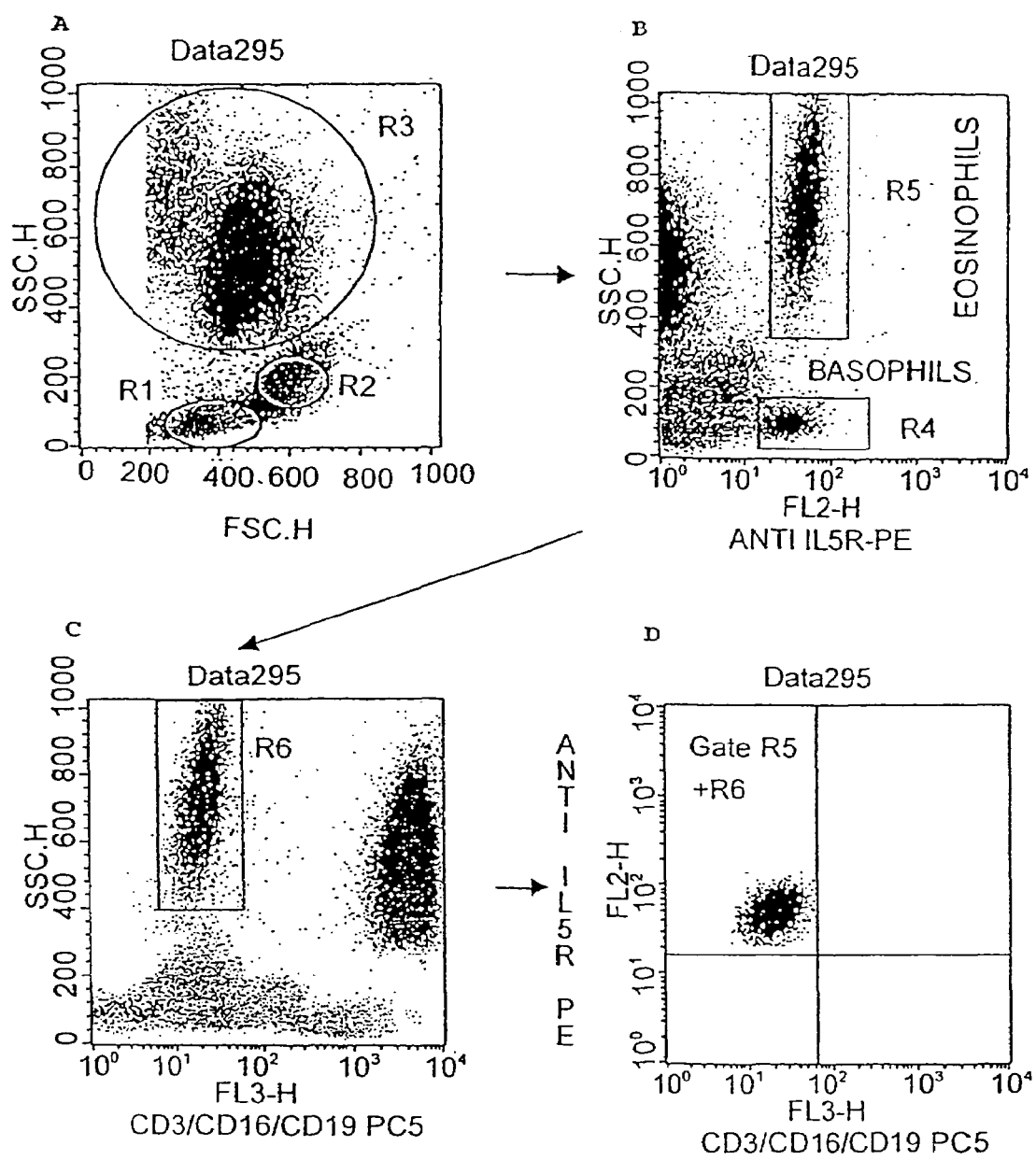

FIG. 3 illustrates a double marking obtained with an anti-IL-5R antibody conjugated to phycoerythrin in combination with a mixture of CD3, CD19 and CD16 antibodies, all conjugated to phycoerythrin-cyanine 5 (PECy5). The FL-1 channel corresponds to the fluorescence emitted by fluorescein, channel FL2 corresponds to the fluorescence emitted by phycoerythrin and channel FL3 corresponds to the fluorescence emitted by phycoerythrin cyanine 5.

Diagram A corresponds to the scatter according to size and particle size distribution. Region R1 which corresponds to lymphocytes, region R2 which corresponds to monocytes and region R3 which corresponds to granulocytes can be distinguished.

Diagram B corresponds to the fluorescence of the anti-IL-5R-PE antibody as a function of side scatter, a function of cell size. R4 corresponds to basophils and R5 to eosinophils.

Diagram C represents the fluorescence of a mixture of anti-CD3, anti-CD16, anti-CD19 antibodies as a function of side scatter. R6 corresponds to unmarked eosinophils.

Diagram D represents the fluorescence of the mixture of anti-CD3, anti-CD16 and anti-CD19 antibodies and the fluorescence of the anti-IL-5R-PE antibody. The eosinophils project into the regions R5 and R6. Only the events present in R5 and R6 are taken into account in diagram D.

Figure 4:
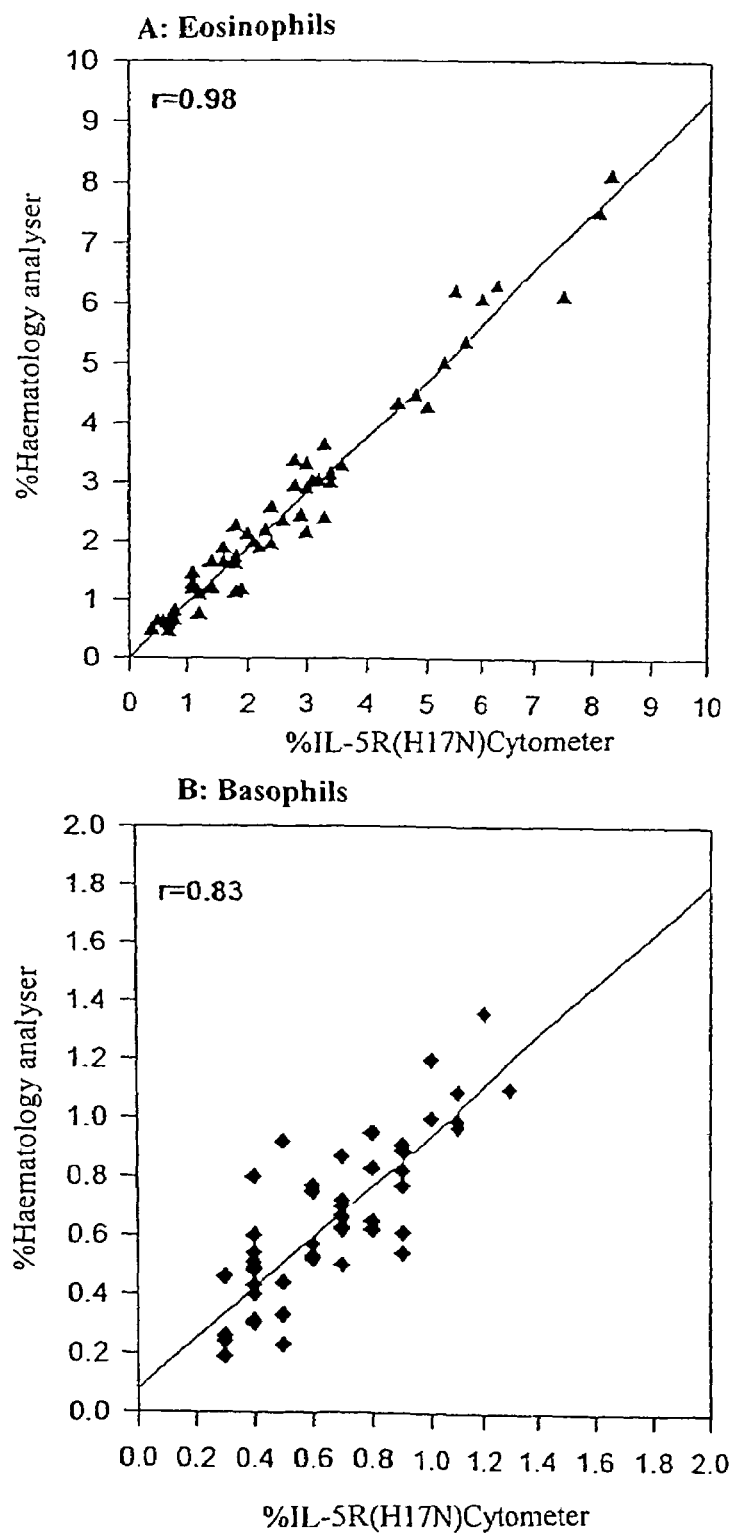

FIG. 4 illustrates the correlation between the percentages given by a haematology analyser and the process of the invention. The abscissas represent the percentage of eosinophils (A) and the percentage of basophils (B) obtained in flow cytometry and the ordinates represent the percentage of eosinophils (A) and the percentage of basophils (B) given by the haematology analyser.

The top graph corresponds to the data obtained for the eosinophils and the bottom graph to the data obtained for basophils. The correlation coefficients are given inside each graph.

FIG. 5A is a typical illustration of a result obtained after activation of the basophils with an anti-IgE antibody.

On this FIG. 5A, dot plot 1 represents the size and particle size distribution of the blood cells, diagram 2 represents the marking obtained with the anti-IL-5R-PE antibody (diagram similar to that shown in FIG. 1), diagram 3 represents the isolation of the basophils and the removal from the population of other possible contaminants such as lymphocytes and monocytes. Diagram 4 represents basophils.

FIG. 5B represents 4 dot plots of activated basophils. Each dot plot corresponds to the stimulation of whole blood by decreasing concentrations of anti-IgE. The cloud of dots of each dot plot corresponds to the population, isolated according to the dot plot 5A-4. The abscissas represent the fluorescence emitted by fluorescein conjugated to the anti-CD63 antibody, and the ordinates represent the fluorescence emitted by phycoerythrin conjugated to the anti-IL-5R antibody.

Figure 6:
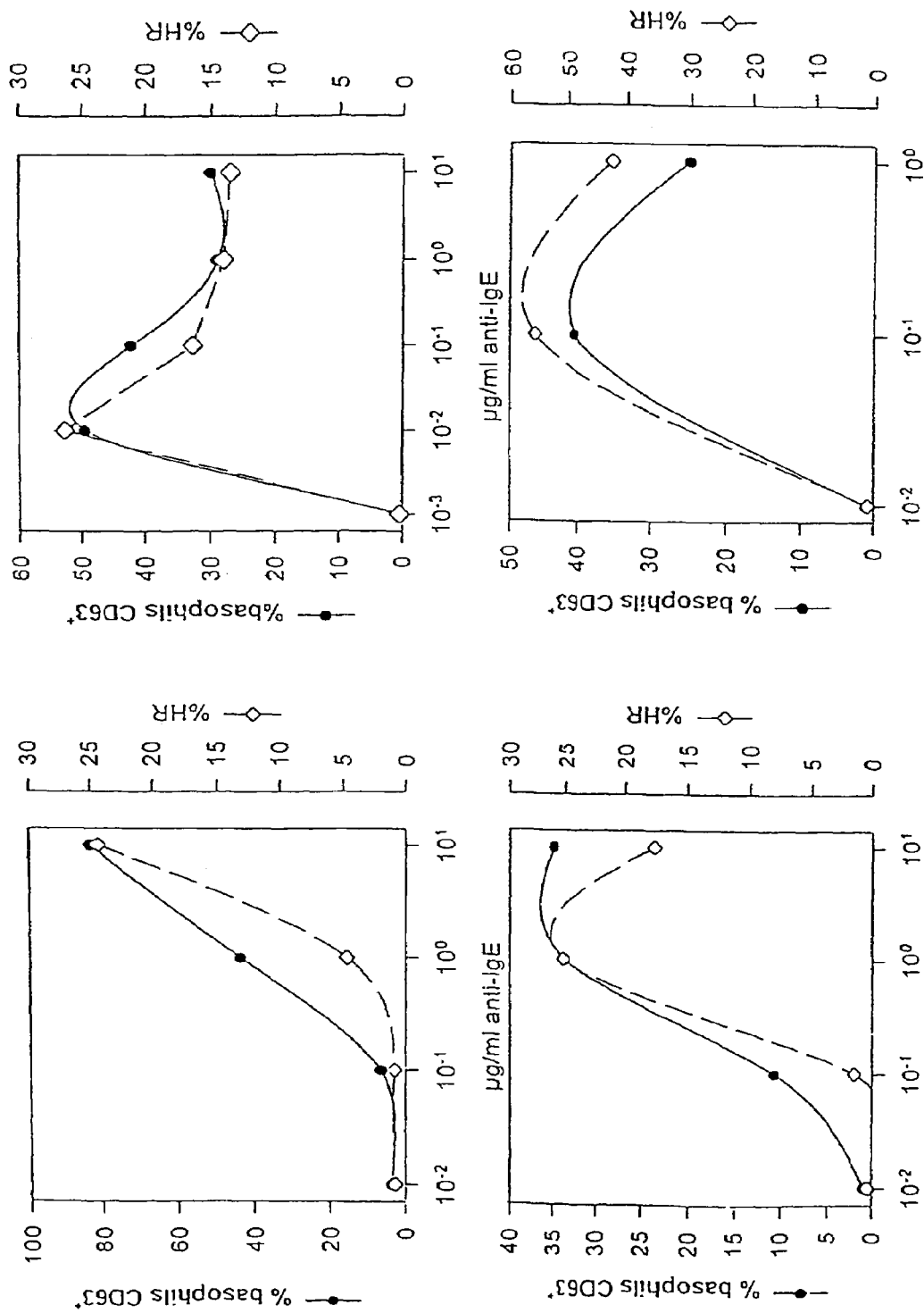

FIG. 6 illustrates the comparison between the percentages of the CD63+IL-5R+ cells and the percentage of histamine released.

Each diagram represents a donor. The black symbols represent the % of CD63+IL-5R+ cells and the white symbols the percentage of histamine released. The abscissas represent the concentration of anti-IgE used by stimulation of the basophils expressed in µg/ml and the ordinates represent the percentage of basophils expressing CD63 or the percentage of histamine released.

Figure 7:
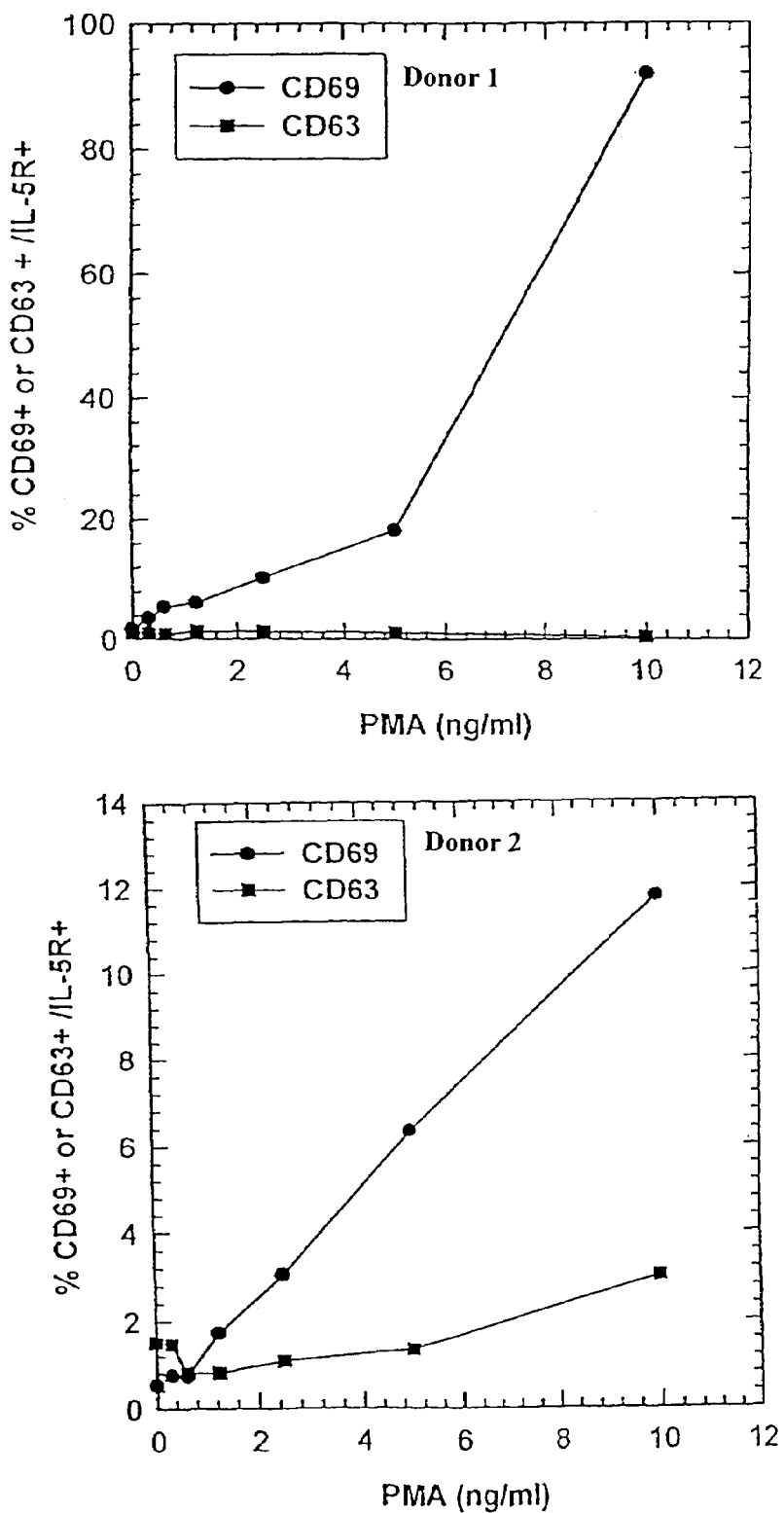

FIG. 7 illustrates the activation of eosinophils by an ester of phorbol (PMA: phorbol myristate acetate). The abscissas represent the concentration of PMA added and the ordinates represent the percentage of eosinophils expressing the CD69 or CD63 molecule. Each diagram represents a different donor.

EXAMPLE 1

Obtaining Anti-IL-5R Monoclonal Antibodies

1. Reagents

Common reagents (salts, buffers etc.) were purchased from Merck, Darmstadt, Germany. The cell culture reagents originate from Bioxyitthaker Virviers, Belgium and from Sigma, Saint-Louis, USA. The anti-CD3, anti-CD16, anti-CD19, anti-CD49d, anti-CD63, anti-CD69 monoclonal antibodies conjugated to fluorescein N-isothiocyanate (FITC) or to phycoerythrin cyanine 5 (PECy5) and the anti-IgE monoclonal antibody clone E124.2.8 are commercial products obtained from Immunotech, Marseilles, France.

2. Fusion

The anti-IL-5R antibody, clone H17N, was obtained after immunisation of mice with a soluble recombinant form of IL-5R, a protein produced from a gene fusion IL-5R-IL-2 and expressed in the CHO cells, then fusion of the blastocytes with the cells of myeloma X63 using the conventional technique described by Köhler and Milstein (1975, Nature 256, 495). The production of antibodies was screened by ELISA using plates covered either with hybrid protein IL-5R-IL-2 or with IL-2. The positive clones on the plates covered with IL-5R-IL-2 and negative clones on plates covered with IL-2 were cloned by limiting dilution. The antibodies were selected on TF-1 cells by virtue of their ability to recognise IL-5R in the presence and in the absence of IL-5, the criterion according to the invention.

Of the monoclonal antibodies selected, the anti-IL-5R monoclonal antibody known as H17N has high affinity for the antigen but does not inhibit the biological activity of IL-5. Consequently, despite the binding of IL-5 to its receptor, no inhibition is observed. The corresponding hybridoma was lodged with the Collection Nationale de Culture de Micro-organismes (CNCM), Institut Pasteur, 28 rue du Dr Roux, 75724 Paris Cédex 15, France on 3 Sep. 1998 under no. 1-2068. The anti-IL-5R monoclonal antibody known as H17N is of the IgG1 type.

3. Conjugation to a Fluorescent Label

The anti-IL-5R antibody H17N was conjugated to phycoerythrin according to the protocol described in "Bioconjugate techniques" by G. Hermanson, Academic Press, 1996.

EXAMPLE 2

Analysis by Cytometry on Whole Blood

1. Blood Samples

The blood samples used for the correlation analysis were obtained from Hôpital La Conception (Marseilles, France). The blood formulation was carried out on tubes containing EDTA as anticoagulant with an STKS-Coulter apparatus, Miami, USA. The blood used for basophil activation was taken using heparin tubes. These samples were taken from persons belonging to the laboratory.

2. Protocol

The expression of IL-5R in different cell sub-populations, from whole blood, was analysed by dual immunolabelling using, on the one hand, anti-IL-5R H17N antibody conjugated to phycoerythrin prepared in stage 3 of example 1 and, on the other hand, markers specific for the cell populations studied.

The protocol used was as follows: 100 µl of whole blood were incubated with 20 µl of anti-IL-5R antibody H17N-PE and 20 µl of a second specific antibody for another marker. The sample was incubated for 15 min at ambient temperature.

Then 1 ml of lysis reagent was added and the reaction mixture mixed vigorously immediately. When the sample became translucent (<1 min), 250 µl of fixing reagent were added and the sample was again mixed carefully. Three ml of isotonic phosphate buffer (PBS 1×) were then added, then the sample was centrifuged for 3 minutes at 1200 rpm. The supernatant was removed by suction and 500 µl of PBS-0.5% formaldehyde were added. The samples were stored at 4° C. in the dark before the cytometer analysis.

Non-specific binding was monitored using an irrelevant antibody of the same isotype reference IM 0670 (Immunotech, Marseilles). This makes it possible to carry out appropriate adjustments to the device. The cytometric analysis of the cells labelled by different fluorochromes was carried out on an FACScalibur apparatus (Becton Dickinson, Mountain View, USA). 100,000 events were analysed for each sample.

3. Identification of Basophils and Eosinophils by Flow Cytometry

The anti-IL-5R H17N antibody was conjugated to phycoerythrin (PE) in order to characterise more easily the cells which express the IL-S receptor. The immunolabelling of whole blood with H17N-PE antibody and a control antibody (irrelevant antibody of the same isotype reference IM 0670) is shown in FIG. 1 (A and B).

In the presence of the control antibody, an absence of marking was observed (FIG. 1A). On the other hand, in the presence of the anti-IL-5R-PE antibody, a time lag of the fluorescence of certain cells was observed (FIG. 1B). The two clouds (windows R5 and R4) of the cells marked by the anti-IL-5R antibody correspond to the eosinophils and basophils. This observation was confirmed thanks to several immunolabelling operations using antibodies specific for different CDs (Clusters of Differentiation). Thus, it was observed that the cells which were positive for IL-5R are negative for the expression of CD3, CD19 and CD16, these CDs being specific for lymphocytes, and negative for the expression of CD14, which is specific for monocytes. However, the cells are positive for CD49d, a protein expressed by eosinophils and basophils, but also by lymphocytes, monocytes and thymocytes.

This shows that the cells marked by the anti-IL-5R antibody correspond well to eosinophils and basophils.

EXAMPLE 3

Quantification of Eosinophils and Basophils

The difference between the percentage of eosinophils and basophils given by the STKS haematology analyser (Coulter, Miami), used in the Hôpital de la Conception in Marseilles, was compared with the percentage of cells which were positive for the expression of IL-5R, detected by the anti-IL-5R H17N antibody according to the invention.

Basophils and eosinophils are the only types of cells marked by the anti-IL-5R antibody according to the invention, but the cloud of basophils is very close to the cloud of cells corresponding to lymphocytes.

A mixture of anti-CD3, anti-CD16 and anti-CD19 antibodies conjugated to phycoerythrin cyanine 5 was added to the anti-IL-5R antibody conjugated to PE, which made it possible to exclude erratic events. This combination made it possible to obtain more accurate values. By using this method, the percentages of eosinophils and basophils obtained by the two methods for 50 different samples were compared. The results are shown in FIG. 4.

FIG. 4A shows the correlation of the percentages of eosinophils obtained with both techniques. This is [% haematology analyser]=0.94[% cytometer]+0 for n=50. FIG. 4B shows the correlation of percentages of basophils obtained with both techniques. This is [% haematology analyser]=0.86[% cytometer]+0.076 for n=50. A very good correlation was observed between the two methods, r=0.98 and r=0.83, showing the great reliability of the process according to the invention.

EXAMPLE 4

Activation of Basophils

The release of histamine by the activated basophils was carried out on 300 µl aliquots of blood placed in a tube and incubated in the presence of different concentrations of anti-IgE in order to establish a dose-response curve.

The samples were mixed gently and incubated at 37° C. for IS minutes. Cell activation was stopped by adding 300 µl of cold phosphate buffer containing 1 mM EDTA. The tubes were centrifuged at +4° C. for 3 minutes at 1200 rpm. The supernatant was recovered in order to quantify the histamine. The cell residue was resuspended in 300 µl of phosphate buffer, 1 mM EDTA and 100 µl of this cell suspension were analysed after immunolabelling.

Quantification of the histamine released was carried out using a commercial radioimmunoassay (reference 1659, Immunotech, Marseilles, France), following the manufacturer's instructions. Total histamine was determined after cell lysis by dilution of 50 µl of blood in 950 µl of distilled water followed by two freeze-defrost cycles. The histamine released after cell activation is expressed as a percentage of total histamine.

The analysis by flow cytometry was carried out after triple marking on 100 µl of cell residue taken up by PBS with anti-IL5R H17N-PE antibody, anti-CD63-FITC antibody and anti-CD3, anti-CD16, anti-CD19 antibodies, all three conjugated to PECy5. The procedure was identical to that described above. In the same way, the analysis of 100,000 cells was acquired. The percentage of doubly marked cells CD63+ and IL5R+ was determined after cell activation.

Figure 5:
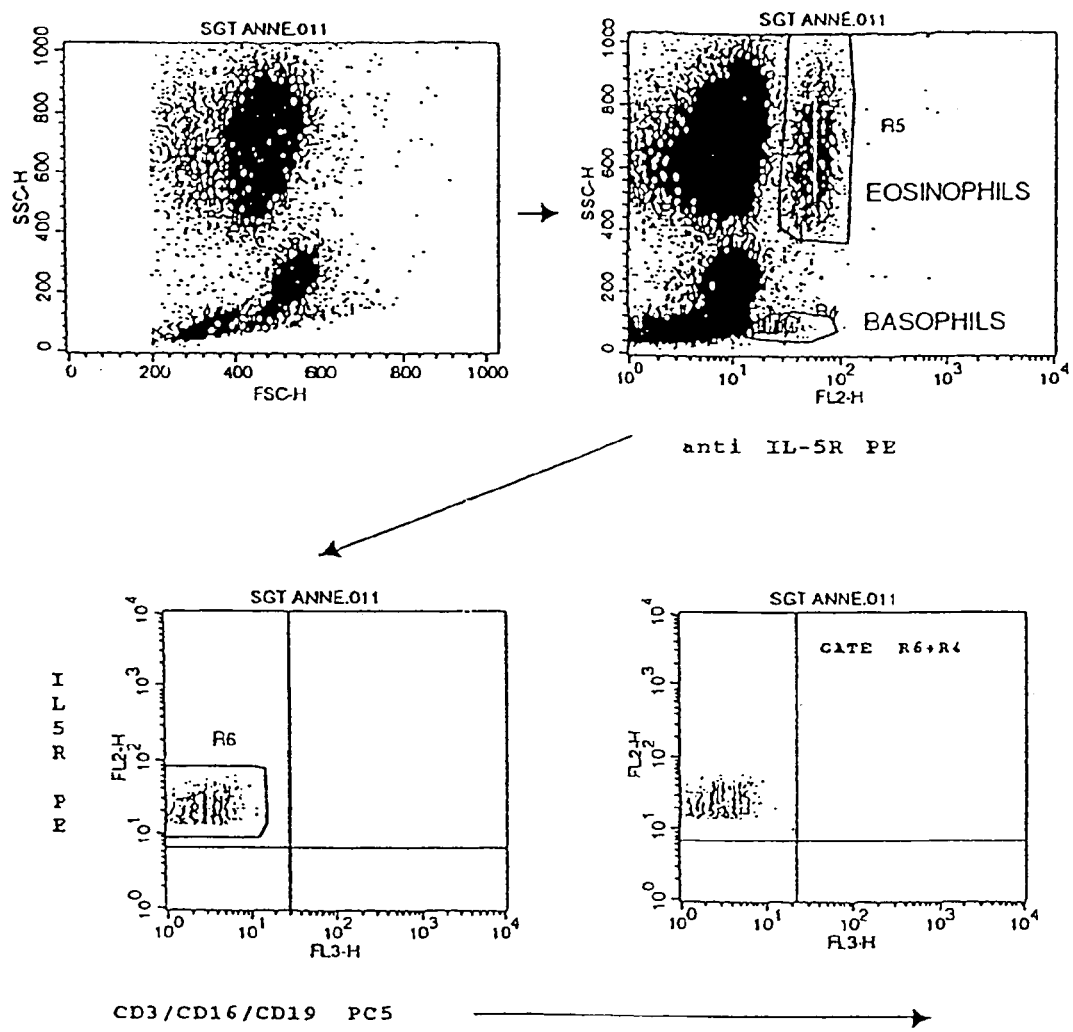
Figure 5:
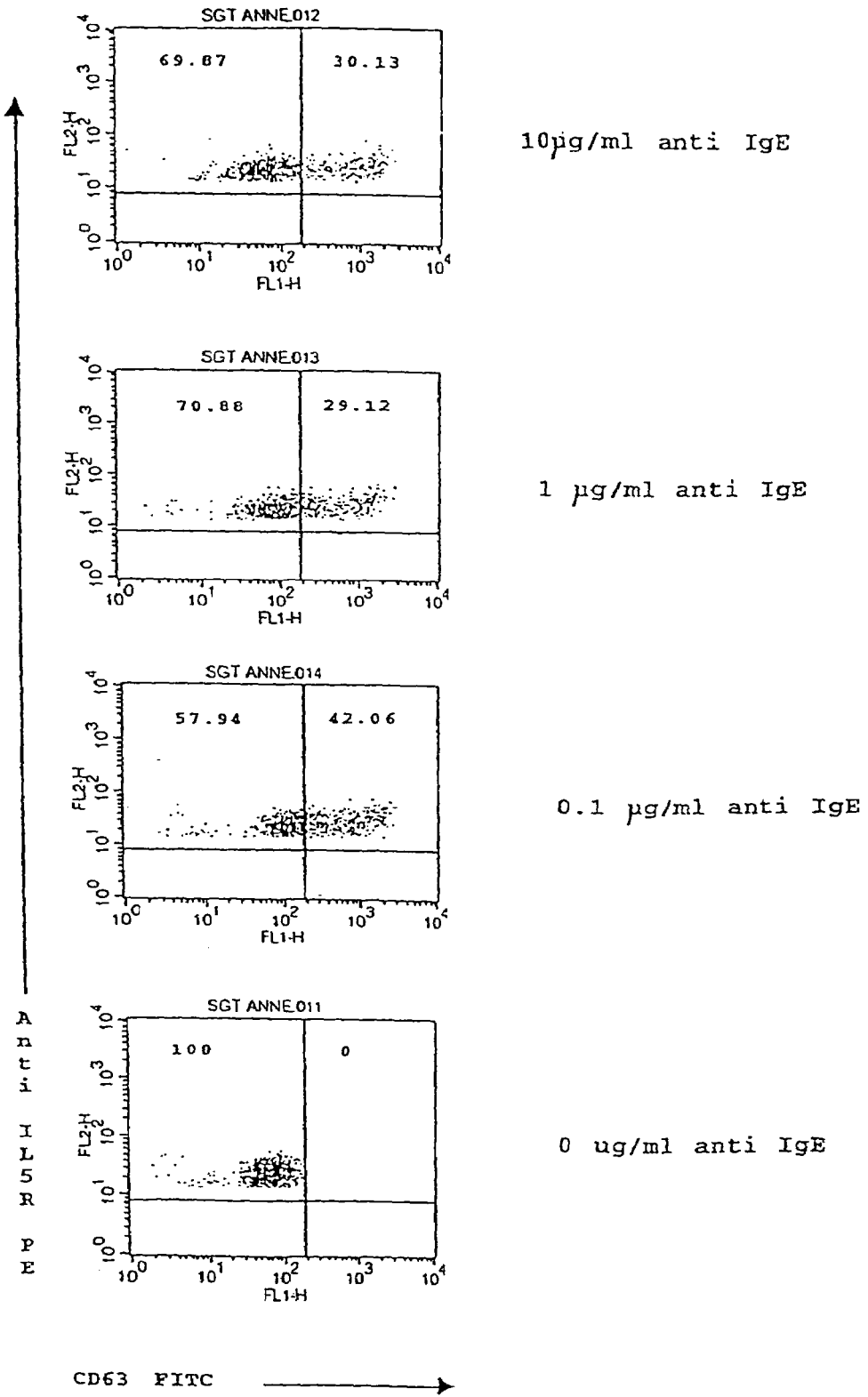

A representative experiment is shown in FIG. 5. An increase in doubly marked cells (CD63 and IL-5R) as a function of the anti-IgE concentration was observed. This increase correlates perfectly with the profile of histamine released, as shown for four different donors in FIG. 6.

EXAMPLE 5

Activation of Eosinophils

The expression of the activation marker CD69 was carried out on 300 µl aliquots of blood placed in a tube and incubated in the presence of different concentrations of PMA (Phorbol Myristate Acetate) in order to establish a dose-response curve. The samples were mixed gently and incubated at 37° C. for 6 hours. Cell activation was stopped by centrifuging at +4° C. for 3 minutes at 1200 rpm. The supernatant was recovered in order to quantify the histamine. The cell residue was resuspended in 300 µl of PBS, 1 mM EDTA and 100 µl of this cell suspension were analysed after immunolabelling.

Quantification of the histamine released was carried out using a commercial radioimmunoassay (reference 1659, Immunotech Marseilles, France), following the manufacturer's instructions. Total histamine was determined after cell lysis by dilution of 50 µl of blood in 950 µl of distilled water followed by two freeze-defrost cycles. The histamine released after cell activation is expressed as a percentage of total histamine.

The analysis by flow cytometry was carried out after triple marking on 100 µl of cell residue taken up by PBS with anti-IL-5R H17N-PE antibody, anti-CD69-FITC antibody or the anti-CD63-FTIC antibody and the anti-CD3, anti-CD16, anti-CD19 antibodies, all three conjugated to PECy5. The procedure was identical to that described above. In the same way, the analysis of 100,000 cells was acquired. The percentage of doubly marked cells CD69+ and IL-5R+ on the one hand, CD63+ and IL5R+ on the other hand, was determined after cell activation.

A representative experiment is shown in FIG. 7. An increase in doubly marked cells (CD69+ and IL-5R+) as a function of the PMA concentration is observed. Interestingly, the marking with the anti-CD63 antibody on the eosinophils did not give any fluorescence showing that CD63 is specific for basophils.

EXAMPLE 6

Kit for the Detection or Quantification of Eosinophils or Basophils

A kit corresponding to the following composition was prepared:
  a vial containing an anti-IL-5R H17N antibody conjugated to phycoerythrin,
  a vial containing a mixture of antibodies:
    anti-CD3 conjugated to PECy5
    anti-CD16 conjugated to PECy5
    anti-CD19 conjugated to PECy5
  a vial containing an "isotype control" antibody conjugated to phycoerythrin
  a vial containing an "isotype control" antibody conjugated to PECy5

EXAMPLE 7

Kit for the Detection or Quantification of Activated Eosinophils or Basophils

A kit corresponding to the following composition was prepared:
  a vial containing an anti-IL-5R H17N antibody conjugated to phycoerythrin,
  a vial containing a mixture of antibodies:
    anti-CD3 conjugated to PECy5
    anti-CD16 conjugated to PECy5
    anti-CD19 conjugated to PECy5
  a vial containing an anti-CD63 antibody conjugated to FITC,
  a vial containing an "isotype control" antibody conjugated to phycoerythrin
  a vial containing an "isotype control" antibody conjugated to PECy5
  a vial containing an "isotype control" antibody conjugated to FITC.

EXAMPLE 8

Kit for the Detection or Quantification of Eosinophils or Basophils

A kit corresponding to the following composition was prepared:
- a vial containing an anti-IL-5R H17N antibody conjugated to phycoerythrin,
- a vial containing a mixture of antibodies:
  - anti-CD3 conjugated to PECy5
  - anti-CD 16 conjugated to PECy5
  - anti-CD19 conjugated to PECy5
- a vial containing an "isotype control" antibody conjugated to PECy5
- a vial containing dichlorofluorescein diacetate.

The invention claimed is:

1. A process for detection or quantification of eosinophils and basophils, comprising:
   bringing a sample, into contact with an IL-5 anti-receptor (alpha chain) monoclonal antibody produced by a hybridoma deposited with the Collection Nationale de Culture de Microorganisme (CNCM) under accession no. I-2068; and
   detecting, and optionally quantifying, any eosinophils and basophils in said sample.

2. A process according to claim 1, wherein the IL-5 anti-receptor monoclonal antibody is an antibody which does not interfere with IgE.

3. A process according to claim 1 or 2, wherein the IL-5 anti-receptor monoclonal antibody is an antibody which does not interfere with the cell activation of eosinophils or basophils.

4. A process according to claim 1 or 2, wherein the detecting step uses a flow cytometer or optical scanning cytometer.

5. A process according to claim 1 or 2, further comprising, for detecting and optionally quantifying activated basophils, bringing the sample into contact with one or more other monoclonal antibodies directed against basophil activation markers.

6. A process according to claim 5, wherein the activation marker is the CD63 antigen.

7. A process according to claim 1 or 2, further comprising, for detecting and optionally quantifying activated eosinophils, bringing the sample into contact with one or more other monoclonal antibodies directed against eosinophil activation markers.

8. A process for the detection and quantification of activated eosinophils according to claim 7, wherein the activation marker is the CD69 antigen.

9. A process according to claim 1 or 2, wherein the IL-5 anti-receptor monoclonal antibody is an antibody of the IgG1 type, produced by the hybridoma which was deposited with the Collection Nationale de Culture de Micro-organismes (CNCM) under accession no. I-2068.

10. A process according to claim 1 or 2, further comprising bringing the sample into contact with other monoclonal antibodies directed against other markers not expressed by eosinophils or basophils.

11. A process according to claim 10, wherein the other monoclonal antibodies are directed against markers CD3, CD16 and CD19.

12. A process according to claim 1, wherein said monoclonal antibody was previously conjugated with a fluorochrome.

13. An IL-5 anti-receptor monoclonal antibody produced by a hybridoma deposited with the Collection Nationale de Culture de Micro-organismes (CNCM) under accession no. I-2068.

14. A kit for the detection or quantification of eosinophils and basophils, comprising:
   an anti-IL-5R monoclonal antibody according to claim 9 conjugated to a first fluorochrome; and
   a mixture of antibody markers for lymphocytes, monocytes and neutrophils, conjugated to a second fluorochrome.

15. A kit for the detection and quantification of activated eosinophils and basophils, comprising:
   an anti-IL-5R monoclonal antibody according to claim 9 conjugated to a first fluorochrome;
   a mixture of antibody markers for lymphocytes, monocytes and neutrophils, conjugated to a second fluorochrome; and
   antibodies directed against activation markers and conjugated to a third fluorochrome.

16. A kit for detection or quantification of the oxidative activity of eosinophils or basophils, comprising:
   an anti-IL-5R monoclonal antibody according to claim 9 conjugated to a first fluorochrome;
   a mixture of antibody markers for lymphocytes, monocytes and neutrophils, conjugated to a second fluorochrome; and
   a marker substrate for oxidative activity of eosinophils or basophils.

17. A kit according to claim 15 or 16, which is applied to a study of allergic, parasitic or leukaemic pathologies.

18. An anti-IL-5R antibody which is characterized by:
   binding to both eosinophils and basophils;
   absence of interference with the fixing of IL-5 to its receptor;
   absence of interference with IgE;
   absence of interference with cell activation of eosinophils or basophils; and
   absence of inhibition of biological activity of IL5, which is produced by a hybridoma deposited with the Collection Nationale de Cultures de Microorganisme (CNCM) under accession no. I-2068.

* * * * *